United States Patent [19]

Tchen et al.

[11] Patent Number: 5,098,825
[45] Date of Patent: Mar. 24, 1992

[54] PROBE CONTAINING A MODIFIED NUCLEIC ACID RECOGNIZABLE BY SPECIFIC ANTIBODIES AND USE OF THIS PROBE TO DETECT AND CHARACTERIZE A HOMOLOGOUS DNA SEQUENCE

[75] Inventors: Paul Tchen, Nanterre; Philip Kourilsky, Paris; Marc Leng, St Cyr; Anne B. Cami, Paris, all of France

[73] Assignee: Institut Pasteur, Paris, France

[21] Appl. No.: 512,602

[22] Filed: Apr. 24, 1990

Related U.S. Application Data

[63] Continuation of Ser. No. 245,952, Sep. 15, 1988, abandoned, which is a continuation of Ser. No. 525,269, Aug. 23, 1983, abandoned.

[30] Foreign Application Priority Data

Dec. 23, 1981 [FR] France ............... 81 24131

[51] Int. Cl.$^5$ .................................... C12Q 1/68
[52] U.S. Cl. ........................... 435/6; 435/71; 435/810; 436/501; 436/804; 436/808; 436/828; 530/389.1; 530/389.8; 935/78; 935/81
[58] Field of Search .............. 435/6, 7.1, 810; 436/501, 828, 804, 808; 935/78, 81; 530/387

[56] References Cited

U.S. PATENT DOCUMENTS

| | | | |
|---|---|---|---|
| 4,061,466 | 12/1977 | Sjohölm et al. | 436/828 X |
| 4,166,104 | 8/1979 | Wagner et al. | 436/539 X |
| 4,358,535 | 11/1982 | Falkow et al. | 435/36 X |
| 4,459,359 | 7/1984 | Neurath | 436/828 X |
| 4,493,899 | 1/1985 | Smith et al. | 436/811 X |

FOREIGN PATENT DOCUMENTS 2019408 of 1979 United Kingdom.

OTHER PUBLICATIONS

Sage et al., Biochemistry, vol. 18, No. 7, pp. 1328–1332.
Spodheim-Maurizot et al., Chemical Abstracts, vol. 94 97632j (1981).
Leng et al., Chemical Abstracts, vol. 89, No. 21, 174795r (1978).
Guigues et al., Chemical Abstracts, vol. 91, No. 5, 33858t (1979).
Grunberger et al., Coding and Conformational Properties of Oligonucleotides Modified with the Carcinogen N-2-Acetylaminofluorene, PNAS 66, 488–494 (1970).
Fuchs et al., Physical Studies on Deoxyribonucleic Acid after Covalent Binding of a Carcinogen, Biochemistry 11, 2659–2666 (1972).
Fuchs et al., Dynamic Structure of DNA Modified with the Carcinogen N-Acetoxy-N-2-acetylaminofluorene, Biochemistry 13, 4435–4440 (1974).
Fuchs, In Vitro Recognition of Carcinogen-Induced Local Denaturation Sites in Native DNA by S1 Endonuclease from Aspergillus Oryzae, Nature 257, 151–152 (1975).
Fuchs et al., Comparative Orientation of the Fluorene Residue in Native DNA Modified by N-Acetoxy-N-2-Acetylaminofluorene and Two 7-Halogeno Derivatives, Biochemistry 15, 3347–3351 (1976).
de Murcia, G. et al., Proc. Nat'l Acad. Sci., vol. 76, 1979, pp. 6076–6080.
Sage et al., Biochemistry, vol. 18, No. 7, pp. 1328–1332 (1979).

*Primary Examiner*—Amelia Burgess Yarbrough
*Attorney, Agent, or Firm*—Finnegan, Henderson, Farabow, Garrett & Dunner

[57] ABSTRACT

A method and kit for detecting a predetermined nucleotide sequence in a specimen using a nucleic acid probe modified with N-2-acetylaminofluorene (AAF).

14 Claims, No Drawings

PROBE CONTAINING A MODIFIED NUCLEIC ACID RECOGNIZABLE BY SPECIFIC ANTIBODIES AND USE OF THIS PROBE TO DETECT AND CHARACTERIZE A HOMOLOGOUS DNA SEQUENCE

This application is a continuation of application Ser. No. 245,952, filed Sep. 15, 1988 now abandoned, which is a continuation of Ser. No. 06/525,269, filed Aug. 23, 1983, now abandoned.

The invention relates to a probe containing a modified nucleic acid recognisable by specific antibodies and to the use of this probe to detect and characterise a homologous DNA sequence in a specimen which can contain it. More particularly the invention relates to a probe chemically modified so that it can, after hybridization with the homologous DNA sequence sought, be detected by antibodies specific with respect to the probe itself.

It is known that DNA's can react under suitable conditions with carcinogenic substances, such as N-acetoxy-N-2-acetylaminofluorene, to form a product which can be recognised by antibodies formed, on the one hand, against N-2 (guanosine-8-yl)-acetylaminofluorene and, on the other hand, against the same DNA's modified by N-acetoxy-N-2-acetylaminafluorene. These techniques have particularly been described in an article of Gilbert de Murcia and collaborators entitled "Visualisation by electronic microscopy of fixation sites of N-acetoxy-N-2-acetylaminofluorene on a DNA of ColE 1 by means of specific antibodies" (Proc. Natl. Acad. Sci USA, volume 76, No. 12, 6 076-6 080 Dec. 1979)."

Under the conditions described by these authors it is possible to modify from 0.07 to 0.15% of the bases of the DNA treated with N-acetoxy-N-2-acetylaminofluorene, the fixation points of the latter chemical substance on the DNA being then locatable by electronic microscopy, after prior reaction of the DNA so modified with the antibodies of the above-indicated type previously formed in the rabbit, then with anti-immunogobulins of rabbits marked with ferritine. The technique described consequently enables healthy native DNA's to be distinguished from DNA's which have been subjected to the action of carcinogenic substances.

The invention is based on a discovery that the modification of a DNA sequence by N-acetoxy-N-2-acetylamino-fluorene would not alter, after prior denaturation of this modified DNA, its capacity to be hybridized with a complementary DNA sequence not bearing such modification groups, when these sequences are placed under conditions enabling such hybridation. The invention takes advantage of this discovery to propose an improved method for detecting the possible presence and characterisation of a sequence or of a particular nucleic acid fragment, particularly of a gene within a composition which can contain it.

The method according to the invention is characterised in that there is placed in contact with the composition presumed to contain a suequence or a certain nucleic acid fragment, a probe containing a complementary nucleic acid which can be hybridized with the nucleic acid sequence or the gene sought, the probe being more particularly characterised in that it bears at least one N-2-acetylaminofluorene group fixed covalently to at least one of the bases of this probe, the possible presence of the nucleic acid sequence or of the gene sought being then developable by an antibody action effective with respect to N-2-(guanosine-8-yl)-acetylaminofluorene or previously prepared with respect to the probe bearing acetylaminofluorene residues (called below DNA-AAF).

It goes without saying that the method claimed within the scope of the present application extends to the use of any other chemical group fixable to a DNA under the conditions described by Murcia et coll.

Naturally, it is self-evident that the DNA-AAF used as a probe is placed in the presence of the DNA to be studied under conditions enabling the re-pairing of complementary sequences, which involves naturally prior denaturisation under well-known conditions of DNA's which can be mutually hybrided.

After hybridization, the DNA-AAF not hybridized specifically is preferably removed by rinsing before proceeding with the detection of the hybrids formed, particularly by placing them in the presence of anti-DNA-AAF antibodies, which can then be fixed to the probe modified and hybridized at the same time with the DNA sequence sought, when the latter was present in the composition used.

After rinsing of the excess antibodies still present, the fixed antibodies may be, either precipitated or developed.

Preferably, development is done by means of an anti-DNA-AAF antibody, advantageously marked by an enzyme of which it is then possible to detect or determine the activity with respect to a specific substrate. Advantageously, those enzymes will be used which are capable of inducing a color reaction at the level of the corresponding substrates.

Development by means of enzymes giving color reaction is very rapid.

The method is very sensitive, especially if amplifying systems (beads, trees or balls of antibodies associated with the enzymes), are used, so that it enables the localization of the genes after hybridization in situ on chromosomes, for example in the case of pre-natal diagnosis.

The method can be quantitative, by measurement of the intensity of the color.

Additional characteristics of the invention with appear also in the course of the description which follows of a typical example of employing the method according to the invention.

Use is made of the following materials and methods:

The DNA's

DNA of pBR 322 phage bearing a sequence of hamster ribosome gene of 6.6 kb inserted at the EcoRI site (clone PWE 6)

separate DNA of phage λ 57 as negative control.

DNA Treated with AAF (DNA-AAF)

The DNA of the clone PWE6 was linearized (by Sal I restriction enzyme) and treated with AAF by the technique described by G. de Murcia et al. (PNAS vol. 76, No. 12 p. 6 076–6 080 1979). The number of modified guanines was estimated at 2% of the number of pairs of bases by measurement of the optical density at 305 nm and 260 nm.

Antibodies

DNA-AAF serum obtained by immunization of a rabbit

Anti-Guo-AAF rabbit antibodies purified on an affinity column rabbit anti-IgG goat antibody linked to peroxydase.

The antibodies were obtained under the conditions described in the above-mentioned article.

Detection Test of DNA-AAF

Variable amounts of DNA-AAF were deposited on nitrocellulose filters (Schleicher and Schüll, type BA 85) of 5 mm diameter.

The DNA had previously been diluted in a 2×SSC solution and denaturated at 100° C., for 5 minutes.

After deposition, the membranes were placed in the oven at 80° C. for 2 hours.

The membranes were then treated with a 3% bovine albumin solution (SIGMA ref. A. 7888), 1, SSC, at 40° C. for one hour, then incubated 30 minutes at ambiant temperature in the same solution in the presence of anti-DNA-AAF antibodies or anti-Guo-AAF of rabbit at a final 2 µg ml.

After incubation, the membranes were washed seven times with PBS, at ambiant temperature, then left to incubate 30 minutes in a 3% bovine alumbin solution, 1 SSC containing rabbit IgG goat antibodies linked to peroxydase at 2 µg/ml final.

After washing seven times with PBS, the color reaction was done by the addition of the following solution, prepared extemporaneously:

2 mg of 3-amino 9 ethylcarbazol (SIGMA ref. A 5754) dissolved in 0.5 ml of N-N' dimethyl formamide, 9.5 ml of 0.05 M pH 5.1 acetic acetate buffer, 10 µl of $H_2O_2$ (Merk ref. 7209)

Hyridization Test with DNA-AAF Used as a Probe

Deposition of variable amounts of DNA PWE 6:
1) 100 ng
2) 10 ng
3) 1 ng
4) 100 ng After deposition, the filters were placed at 80° C. for 2 hours, then prehybridated 4 hours at 68° C. in a 6×SSC solution and 10×Denhardt. (1×Denhardt containing:

0.02% of Polyvinyl pyrollidone, 0.02% of the reagent marketed under the name Ficolle 400 by "Pharmacia fine Chemicals".

0.02% of bovine albumin)

They were then hybridized in a 2×SSC 1×Denhardt solution in the presence of 200 µl per membrane of DNA-AAF solution previously denaturated containing respectively:

10 ng/ml final 1 ng/ml final and 100 pg/ml final

After hybridization, the filters were washed 30 minutes in 2×SSC 1 Denhardt 30 minutes in 1×SSC 1 Denhardt 30 minutes in 0.5×SSC 1 Denhardt 30 minutes in 0.2×SSC 1 Denhardt 1 hour 0.1×SSC 1 Denhardt then incubated for one hour at 40° C. in a solution containing 3% of albumin at 1×SSC. The subsequent operations were carried out as previously (contacting with anti-DNA-AAF or anti Guo-AAF antibodies, PBS washing, antibodies+peroxydase, PBS washing and development).

After development colored spots were observed whose intensity (greater for high concentration, weaker for low concentration DNA) depends on the amount of hybridized DNA.

The above-indicated detection method had lead to entirely negative results at the end of hybridation tests carried out between the negative control (used in amounts reaching 90 nanograms) and the DNA-AAF.

The invention is obviously not limited to the embodiments described above by way of example and one skilled in the art can introduce therein modifications without however departing from the scope of the following claims.

As modifications usable at the level of the detection of hybrids formed with the probe according to the invention, will be cited:

the development of the hybrids formed by radioactivity, for example by the use of anti-DNA-AAF antibodies rendered radio-active by iodine 125 or 131 or radio-active protein A, which will be fixed on the antibodies.

Finally, by way of possible variations in the uses, will be mentioned the application of the probe according to the invention to the purificaton of a complementary DNA contained in an initial composition, particularly by means of protein A associated with a solid support (for example constituted by agarose beads), of precipitating antibodies associated or not with a solid support (beads of agarose, of latex, etc.), to ensure the selective precipitation of the hybrid formed.

Finally forming part of the modificatons remaining within the scope of the claims is the possible substitution of the AAF by any carcinogenic equivalent molecule or the like capable of being fixed under the same conditions to certain at least of the bases of the nucleotides from which the probe is constituted.

We claim:

1. A kit for the detection or isolation of a first predetermined nucleotide sequence in a specimen, comprising:

a probe containing a second nucleotide sequence which is complementary to said first predetermined nucleotide sequence and which can be hybridized with said first predetermined nucleotide sequence; said probe further containing a N-2-acetylaminofluorene group covalently fixed to a base of said second complementary nucleotide sequence; and first antibodies formed against N-2-(guanosine-8-yl)-acetylaminofluorene or against a nucleotide sequence covalently fixed to an N-2-acetylaminofluorene group.

2. The kit of claim 1, which further comprises means for developing said first antibodies.

3. The kit of claim 2, wherein said developing means comprise second antibodies which bear an enzyme.

4. The kit of claim 3, wherein said enzyme can give a color reaction.

5. The kit of claim 1, which further comprises protein A on a solid support for precipitating, from said specimen, a hybrid of said first predetermined nucleotide sequence and said probe fixed to said first antibodies.

6. The kit of claim 1, wherein said first antibodies are provided on a solid support for precipitating, from said specimen, a hybrid of said first predetermined nucleotide sequence and said probe.

7. The kit of claim 1, wherein said first and second nucleotide sequences are DNA sequences.

8. A method for detecting a first predetermined nucleotide sequence in a specimen, comprising:
   contacting said speciment, under hybridization conditions, with said probe of said kit of claim 1 to form a hybrid of said probe and said first predetermined nucleotide sequence; and then
   contacting said hybrid with said first antibodies of said kit of claim 1 to fix said first antibodies to said hybrid.

9. The method of claim 8, which further comprises precipitating, from said specimen, said hybrid fixed to said first antibodies by contacting said hybrid with protein A on a solid support.

10. The method of claim 8, wherein said first antibodies are on a solid support so that said hybrid precipitates from said specimen.

11. The method of claim 8, which further comprises developing said first antibodies.

12. The method of claim 11, wherein said first antibodies are developed by treating said hybrid fixed to said first antibodies with second antibodies which bear an enzyme.

13. The method of claim 12, wherein said enzyme can give a color reaction.

14. A method for detecting a first predetermined DNA nucleotide sequence in a specimen, wherein the method comprises:
   contacting said specimen, under hybridization conditions, with a probe containing a second DNA nucleotide sequence which is complementary to said first predetermined DNA nucleotide sequence to form a hybrid of said probe and said first predetermined DNA nucleotide sequence; said probe further containing a N-2-acetylaminofluorene group covalently fixed to a base of said second complementary DNA nucleotide sequence;
   contacting said hybrid with antibodies formed against N-2-(guanosine-8-yl)-acetylaminofluorene or against a nucleotide sequence covalently fixed to an N-2-acetylaminofluorene group to thereby form an antibody-antigen complex, wherein said antibodies have bound thereto an immunological label selected from the group consisting of radioactive and enzymatic labels; and
   detecting the label bound to the antibodies.

* * * * *